United States Patent [19]

Boebel et al.

[11] Patent Number: 4,985,033
[45] Date of Patent: Jan. 15, 1991

[54] APPARATUS FOR FIXING FASCIAL HOLDING SUTURES IN OPEN LAPAROSCOPY

[75] Inventors: Manfred Boebel, Oetisheim; Henning Becker, Neunkirchen, both of Fed. Rep. of Germany

[73] Assignee: Richard Wolf GmbH, Knittlingen, Fed. Rep. of Germany

[21] Appl. No.: 486,464

[22] Filed: Feb. 28, 1990

[30] Foreign Application Priority Data

May 12, 1989 [DE] Fed. Rep. of Germany ....... 3915597

[51] Int. Cl.$^5$ ....................... A61B 17/00; A61M 5/32
[52] U.S. Cl. .................................. 606/148; 604/174; 604/283; 604/905
[58] Field of Search ............... 606/148, 108, 198, 190; 604/175, 164, 104, 165, 174, 283, 905; 128/DIG. 26

[56] References Cited

U.S. PATENT DOCUMENTS

| 3,817,251 | 6/1974 | Hasson | 604/42 |
| 4,419,094 | 12/1983 | Patel | 604/174 |
| 4,617,933 | 10/1986 | Hasson | 606/190 |
| 4,834,712 | 5/1989 | Quinn et al. | 604/174 |
| 4,834,719 | 5/1989 | Arenas | 604/174 |

*Primary Examiner*—Randall L. Green
*Assistant Examiner*—Gary Jackson
*Attorney, Agent, or Firm*—Panitch Schwarze Jacobs & Nadel

[57] ABSTRACT

Apparatus for fixing fascial holding sutures in open laparoscopy defines a central channel which allows it to be slipped onto, and fixed in position on, a trocar canula holding a laparoscope. A push-pull rod is radially displaceable by means of a hand lever, for detachably clamping the fixing apparatus to the trocar canula. The apparatus basically comprises a tapered seal and a retaining plate which is detachably connected thereto and has at several points thereon manually operable clamping devices for securing the fascial holding sutures.

8 Claims, 2 Drawing Sheets

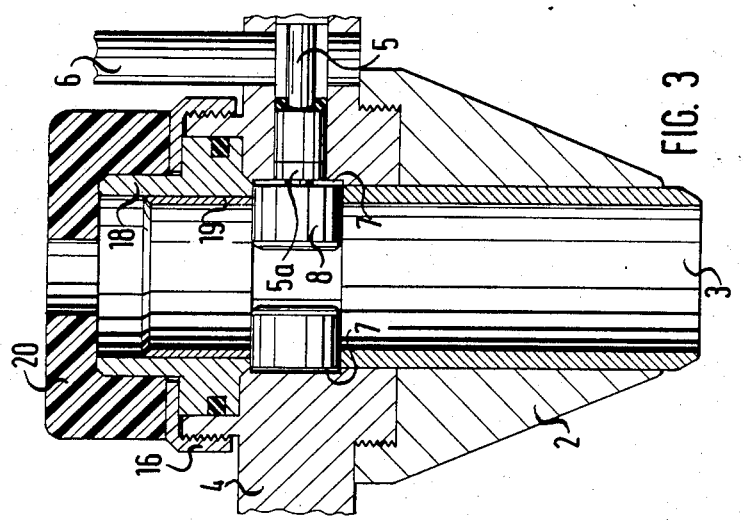
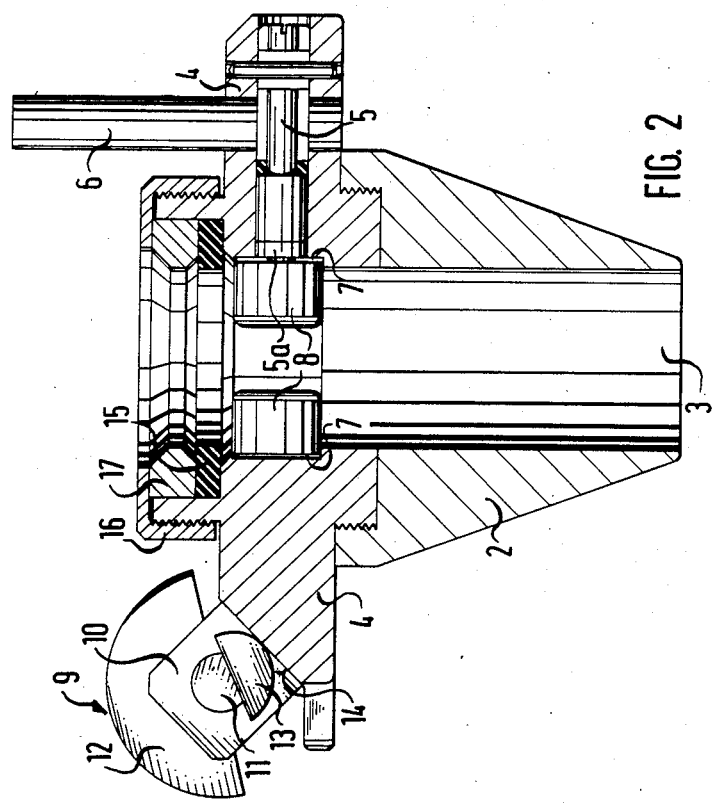

APPARATUS FOR FIXING FASCIAL HOLDING SUTURES IN OPEN LAPAROSCOPY

FIELD OF THE INVENTION

The invention relates to apparatus for fixing fascial holding sutures in open laparoscopy and comprising a tapered seal which is displaceable on a trocar canula, a laparoscope being introducible through said apparatus into the body cavity.

BACKGROUND OF THE INVENTION

A trocar canula which is disclosed in DE-B-3011069, comprises at least two opposed slotted clamps for securing fascial holding sutures, and a freely longitudinally displaceable tapered seal. This trocar canula has the disadvantage that, after its insertion into an opening in the abdominal wall, the trocar canula and the tapered seal assume an unalterable position relative to one another since the said sutures which are firmly connected to the trocar canula determine its position and that of the tapered seal, in the opening in the abdominal wall. The relative positioning of the tapered seal and trocar canula cannot be altered without disturbing their positioning in the opening in the abdominal wall, thereby destroying the gastight closure of the abdominal cavity.

SUMMARY OF THE INVENTION

An object of the invention is to enable the trocar canula to be freely moved into axial positions thereof that are needed during an operation, without the unintentional loss of gas in the abdominal cavity.

According to the present invention in an apparatus for fixing fascial holding sutures, having a tapered seal, for open laparoscopy, with an axial passageway for feeding through and fixing a trocar canula holding a laparoscope, the tapered seal has a retaining plate which is detachably fastenable to its proximal end and a plurality of manually operable clamping devices for detachably fixing the ends of the fascial holding sutures. The tapered seal and the retaining plate with the clamping devices are jointly detachably fastenable to the trocar canula by means of a push rod which is radially displaceable by means of the hand lever and acts upon a tension ring.

The fixing apparatus may be such that it can be used both for normal laparoscopy and for trocar canulae of a different diameter.

BRIEF DESCRIPTION OF THE DRAWINGS

FIG. 2 is an axial section through the fixing apparatus; and

FIG. 3 is a similar view to that of FIG. 2 showing a space reducing bush inserted into the fixing apparatus.

DETAILED DESCRIPTION OF THE INVENTION

Figure 1:
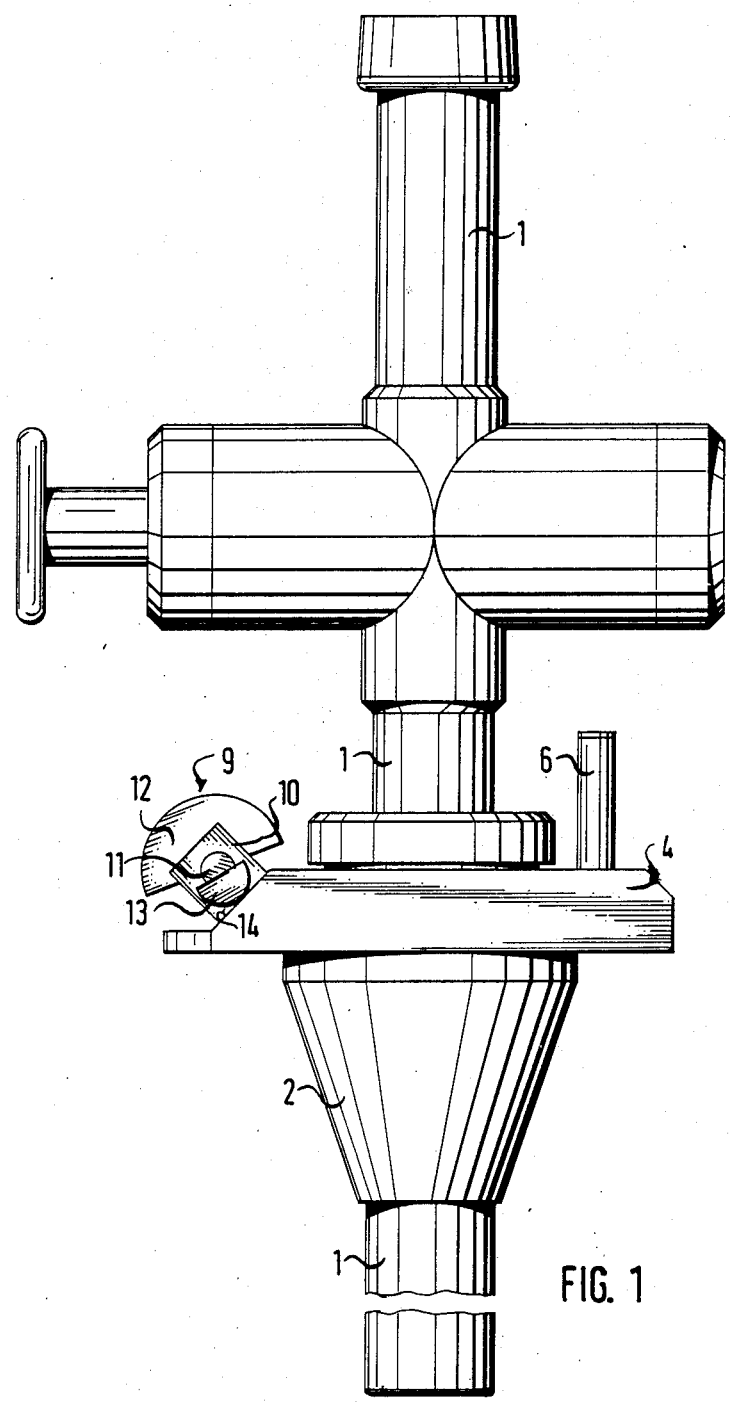
FIG. 1 is a side view of a trocar canula having fixing apparatus according to the invention assembled thereto.

The fixing apparatus which comprises a tapered seal 2 and a annular proximal retaining plate 4, having a central axial channel 3 has as shown in FIG. 3, been slipped onto a trocar canula holding a laporoscope and being provided with a valve, the canula 1 extending through the channel 3. The seal 2 is detachably secured to the retaining plate 4 so that this can be used for normal laporoscopy. For fixedly positioning said apparatus axially on the canula 1, the retaining plate 4 is formed with a radial bore receiving, sealingly and axially adjustably, a push-pull rod 5, having a screw thread meshiing with a screw thread in a transverse bore proximate to an end of a hand lever 6. The lever 6 is immovable axially of the rod 5 but can be swivelled to a limited extent about the axis thereof to push the rod 5 towards the channel 3 to urge a compensating element 5a against a discontinuous, that is to say part annular, tension element 8 which fits loosely in an annular recess 7 in the retaining plate 4. The advance of the rod 5 towards the channel 3 thus causes the tension element 8 to reduce the free lumen of the channel 3 so that the fixing apparatus 2,4 is detachably locked to the canula 1 passed therethrough.

There are provided at several positions on the retaining plate 4, clamping devices 9 for securing fascial holding sutures for retaining the apparatus 2,4 in a fixed position relative to the abdominal wall during laparoscopy.

Each clamping device 9 comprises a bearing block 10 rotatably supporting a shaft 11 provided on one side of the block 10 with a handle 12 for angularly displacing the shaft 11, and on the other side of the block 10, with an eccentric part or cam 13, having a roughened or profiled frictional peripheral cam surface, formed for example with transverse grooves.

The end of said sutures are inserted between the said peripheral surface and a facing, inclined cooperating surface 14 of the retaining plate 4 and are progressively clamped thereto by rotating the cam 13 by means of the handle 12. The cam 13 may be secured in an open position to allow the insertion of the suture ends, by means for example of projection and notch means or a spring loaded ball catch.

The apparatus 2,4 can, by virtue of the structure described above, be easily and comfortably fixed in the opening in the abdominal wall, by means of said fascial sutures. The doctor operating can then shift the trocar canula 1 axially by means of the fixing apparatus 2,4 in order to reposition the canula 1. The apparatus 2,4 however, remains locked in its fixed position by means of said sutures.

The apparatus 2,4 is sealed from the canula 1 by means of a sealing element 15 held in position by means of a screw cap 16 by way of a thrust collar 17.

For adapting the apparatus 2,4 to trocar canulae of various diameters, the cap 16 is unscrewed and the sealing element 15 and the collar 17 are removed. A space reducing bush 18, (FIG. 3), is then inserted into the channel 3 to narrow it and is fixed in position by means of the screw cap 16, the bush 18, having an upper extension as a substitute for the thrust collar 17. The tension element 8 is loosely positioned in the bush 18 by means of a cylindrical sleeve 19. The top of the channel 3 or that of the bush 18 is closed by the sealing element 15 or by a rubber cap 20, respectively. The cap 20 has a central opening the edge of which sealingly engages the canula 1 to prevent the escape of gases from the abdominal cavity.

What is claimed is:

1. Apparatus for fixing fascial holding sutures in open laparoscopy, the apparatus comprising:
   a tapered seal defining an axial passage way for feeding therethrough a trocar canula holding a laporoscope, said seal having a distal end and a proximal end;

a retaining plate detachably securable to the proximal end of the tapered seal;

a plurality of manually operable clamping devices on the retaining plate for detachably fixing ends of said sutures; and a push rod and a tension element in said retaining plate, the push rod having a hand lever for radially displacing the push rod to act upon the tension element detachably to secure the fixing apparatus to the trocar canula.

2. Apparatus as claimed in claim 1, comprising means supporting the hand lever in perpendicular relationship with the push rod, for swivelling movement about the axis thereof, said push rod being formed with a screw thread and said lever having a bore formed with a screw thread meshing with that of the push rod, a compensating element being disposed between the push rod and the tensioning element; whereby the hand lever is swivellable to displace the push rod to act upon the tension element by way of the compensating element.

3. Apparatus as claimed in claim 1, wherein each clamping device comprises a shaft, means supporting the shaft for rotation, a cam connected to the shaft and having a cam surface proximate to a cooperating surface of the retaining plate, and a handle on the shaft for rotating the shaft to fix said suture ends between said cam surface and said cooperating surface.

4. Apparatus as claimed in claim 3, wherein said cam surface is provided with frictional means.

5. Apparatus as claimed in claim 3, wherein said cam surface is formed with transverse grooves.

6. Apparatus as claimed in claim 1, said retaining plate further comprising a cylindrical extension in said axial passageway containing a resilient sealing element; and a thrust collar and a rigid annular cap for retaining said sealing element in position, in said extension.

7. Apparatus as claimed in claim 1, further comprising a space reducing bush which is axially fixable in said axial passageway and has an annular shoulder and a cylindrical recess loosely axially supporting said tension element; and a resilient cap having a central opening, closing the proximal end of said bush.

8. Apparatus as claimed in claim 1, wherein the tapered seal and the retaining plate 1 are detachably fastenable to each other in gas-tight fashion.

* * * * *